(12) United States Patent
Houthoff et al.

(10) Patent No.: US 6,733,983 B1
(45) Date of Patent: May 11, 2004

(54) METHOD FOR IDENTIFYING A MYCOBACTERIUM SPECIES

(75) Inventors: Hendrik-Jan Houthoff, Amsterdam (NL); Saskia Kroon-Swart, Voorschoten (NL); Remco Van Der Meulen, Amsterdam (NL); Soenita Goerdayal, Nieuwegein (NL); Arend Kolk, Muiderberg (NL); Lenka Perira Arias-Bouda, Amstelveen (NL); Sjoukje Kuyper, Amsterdam (NL)

(73) Assignee: Kreatech Biotechnology, B.V., Amsterdam (NL)

( * ) Notice: Subject to any disclaimer, the term of this patent is extended or adjusted under 35 U.S.C. 154(b) by 0 days.

(21) Appl. No.: 09/581,013

(22) PCT Filed: Dec. 8, 1998

(86) PCT No.: PCT/NL98/00701

§ 371 (c)(1),
(2), (4) Date: Jul. 7, 2000

(87) PCT Pub. No.: WO99/30162

PCT Pub. Date: Jun. 17, 1999

(30) Foreign Application Priority Data

Dec. 8, 1997 (EP) .............................................. 97203851

(51) Int. Cl.[7] ...................... G01N 33/554; G01N 33/53; C12Q 1/00; C12N 11/00; A61K 39/04
(52) U.S. Cl. ................ 435/7.32; 424/150.1; 424/163.1; 424/168.1; 424/248.1; 435/4; 435/7.1; 435/174; 435/253.1
(58) Field of Search ........................... 424/150.1, 163.1, 424/168.1, 248.1; 435/4, 7.1, 7.32, 174, 253.1

(56) References Cited

U.S. PATENT DOCUMENTS 4,391,904 A * 7/1983 Litman et al. .................. 435/7
5,817,473 A * 10/1998 Das et al. .................... 435/7.32

FOREIGN PATENT DOCUMENTS

| EP | 0407605 A1 | 1/1991 | |
| WO | WO94/14069 | 6/1994 | ......... G01N/33/569 |
| WO | WO97/09429 | 3/1997 | ........... C12N/15/31 |

OTHER PUBLICATIONS

Araj, G.F.., et al. "Improved Detection of Mycobacterial Antigens in Clinical Specimens by Combined Enzyme–Linked Immunosorbent Assays", Diagn. Microbiol. Infect. Dis., vol. 17, pp. 119–127, 1993.*

Roche, P.W., et al, "Antibody Responses to the 18–kDa Protein of *Mycobacterium leprae* in Leprosy and Tuberculosis Patients", International Journal of Leprosy, vol. 60, No. 2, pp. 201–207, 1992.*

Vega–Lopez et al, Recognition of mycobacerial antigens by sera from patients with leprosy. Journal of Clinical Microbiology. vol. 26, No. 12, pp. 2472–2479. 1988.*

Havlir, D. V. et al., "Human Immune Response to *Mycobacterium Tuberculosis* Antigens." Infection and Immunity (1991) 59:665–670.

Rambukkana, A. et al., "Subcellular Distribution of Monoclonal Antibody Defined Epitopes on Immunodominant *Mycobacterium Tuberculosis* Proteins in the 30–kDa Region: Identification and Localization of 29/33–kDa Doublet Proteins on Mycobacterial Cell Wall". Scandanavian Journal of Immunology (1991) 33:763–775.

Sada et al. "An ELISA for the Serodiagnosis of Tuberculosis Using a 30,000–Da Native Antigen of *Mycobacterium Tuberculosis*" Journal of Infectious Disease (1990) 162:928–931.

G.H. Bothamley, "Serological diagnosis of tuberculosis," European Respiratory Journal (1995) 8:676s–688s.

Brennan, P.J., "Diagnosis of Leprosy based on the 3,6–di–O–methyl–Beta–D–Glyucopyranosyl Epitope Assay of Antibodies with Natural and Synthetic Probes Assay of Antigen by Chemical and Immunological Means," 19th Joint Leprosy Research Conference, Tokyo, Japan (Aug. 27–29, 1984), p. 619, col. 2, line 28–line 31.

* cited by examiner

Primary Examiner—Rodney P Swartz
(74) Attorney, Agent, or Firm—Hoffmann & Baron, LLP

(57) ABSTRACT

The invention relates to a method for identifying a Mycobacterium species comprising the steps of:
  a) contacting at least one immuno-cross reactive antigen component of a mycobacterial species with a sample of a body fluid of a human or animal individual;
  b) contacting at least one antibody, which is capable of reacting with a mycobacterial antigen, with said body fluid sample;
  c) detecting the presence of antigen-antibody complexes, and identifying the Mycobacterium species present in said body fluid sample.

42 Claims, 1 Drawing Sheet

METHOD FOR IDENTIFYING A MYCOBACTERIUM SPECIES

The present application claims the benefit of International patent application serial number PCT/NL98/00701 filed Dec. 8, 1998, which in turn is based on the European patent application serial number EP 97203851.7 filed Dec. 8, 1997.

The invention relates to a method for identifying a Mycobacterium species responsible for a mycobacterial infection in a human or animal, and to diagnostic kits for use in said method.

The genus Mycobacterium contains about 50 species. It is responsible for a number of diseases which are known collectively as mycobacterioses. The best known and widest spread of these are leprosy, caused by *M. leprae*, and tuberculosis caused by *M. tuberculosis*. Both of these diseases affect more than ten million people all over the world. Most other mycobacteria normally occur only as environmental saprophytes. However, they can also cause opportunist diseases, which happens often, but not exclusively, in organisms suffering from problems with their immune systems, such as AIDS patients or people undergoing immunosuppression. The opportunist types comprise the slow-growing species *M. avium*, and the closely related *M. intracellulare* and *M. scrofulaceum* (often together referred to as the MAIS complex), *M. kansai, M. marinum* and *M. ulcerans*, and the fast-growing species *M. chelonae* and *M. fortultum*. Although quite rare in the Western world for several decades, the occurrence of opportunist mycobacterial diseases and tuberculosis has shown a significant increase with the incidence of AIDS. Further, it has been reported that mycobacteria or antigens of mycobacteria play a role in the etiology of a plurality of other diseases, such as sarcoidosis and Crohn's disease, as well as different auto-immune diseases, such as auto-immune dermatitis, rheumatoid arthritis and diabetes. It has been suggested that this role can be attributed to a structural mimicry between epitopes of mycobacteria and those of the host organism.

The cell walls of mycobacteria are very complex and contain many different lipids, some of which have structures unique to the genus. These structures comprise mycolinic acids and esters, peptido-glycolipide, arabino-galactane and lipo-arabinomanane. The lipid-rich cell walls of a mycobacterial cell are responsible for the notable coloring properites of the mycobacteria. They also enable mycobacteria to counter an attack by the immune system of a host organism. A number of species, after being taken up into macrophages, surround themselves with a thick layer of secreted lipids.

Many of the different components of the mycobacteria interact with the immune system of a host organism. These components comprise proteins and hydrocarbon antigens, which can either be actively secreted by the mycobacteria or can form part of the cell wall or cell membrane. In addition, they may be present in the cytoplasm, for example in the cytoplasmic matrix, ribosomes and enzymes. Mycobacteria further also possess immuno-modulating components, such as immunosuppressing compounds and adjuvants. As of consequence, a single mycobacterial species can induce a large variety of immune responses in different forms having diverse specificities. This makes it very difficult to derive protein antigens which are suitable for the detection of species-specific humoral responses as a basis for a highly sensitive and specific diagnostic test for the above mentioned diseases, particularly tuberculosis. Because mycobacteria have a frequent occurrence, both human and animal body fluids contain nearly at all times anti-mycobacterial antibodies.

In the past, researchers have attempted to develop a sufficiently sensitive diagnostic test for mycobacterioses. The focus of these attempts has mostly been on finding species-specific glycolipid antigens for the detection of specific humoral immune responses, because of the problems with the specificity of protein antigens.

In the international patent application 94/14069, it has been disclosed to make use of the antibody response of an organism to immuno-dominant mycobacterial cross-reactive antigen components (further referred to as Im-CRAC) for developing a diagnostic test for mycobacterial infections. The Im-CRAC is believed to provide indirect information on the nature of the immune recognition of, and response to, a specific mycobacterial pathogen.

The method proposed in WO-A-94/14069 is based on the discovery that the clinical manifestation of mycobacterial diseases is related to the varying capability of an individual host to produce a humoral response to different mycobacterial immuno-cross-reactive antigen components (Im-CRAC). Each mycobacterial infection generates its own specific antibody response to a number of specified antigens. Analysis of the antibody-response, e.g. by immunoblotting, has demonstrated that the immuno-dominant Im-CRAC vary in accordance with the immunopathological manifestation of the mycobacterial diseases. Said analysis results in different and distinguishing band patterns of mycobacterial antigens for different individuals which are infected with different Mycobacterium species. The band pattern, which is obtained after an immunoblot, can be referred to as an Antigen Bar Code. The antigen-antibody reactions which are shown in the bar code are, when taken together, unique for a certain Mycobacterium species.

The present invention aims at providing an improved method for identifying a Mycobacterium species in a diagnostic test. Although satisfactory in most aspects, it is still desirable to have a diagnostic test which is even more sensitive than the method described in WO-A-94/14069. Furthermore, there is a need for a diagnostic test which can be used in the determination of previous vaccination, and for monitoring therapy of organisms infected with a Mycobacterium species. During therapy, there are situations where low levels of certain antibodies occur, which may disturb the accuracy and/or sensitivity of the test making use of the antibody-antigen cross-reactions, as outlined hereinabove.

SUMMARY OF THE INVENTION

It has now been found that a highly sensitive diagnostic test can be performed by contacting a sample of a body fluid with both antibodies and antigens. It has been found that, besides antibodies, several mycobacterial components are present in animal and human body fluids, of which the presence can be determined by using cross-reactions with a chosen set of antibodies in a reliable manner.

The invention therefore provides a method for identifying a Mycobacterium species comprising the steps of:
a) contacting at least one immuno-cross reactive antigen component of a mycobacterial species with a sample of a body fluid of a human or animal individual;
b) contacting at least one antibody, which is capable of reacting with a mycobacterial antigen, with said body fluid sample;
c) detecting the presence of antigen-antibody complexes, and identifying the Mycobacterium species present in said body fluid sample.

DETAILED DESCRIPTION OF THE INVENTION

Figure 1:
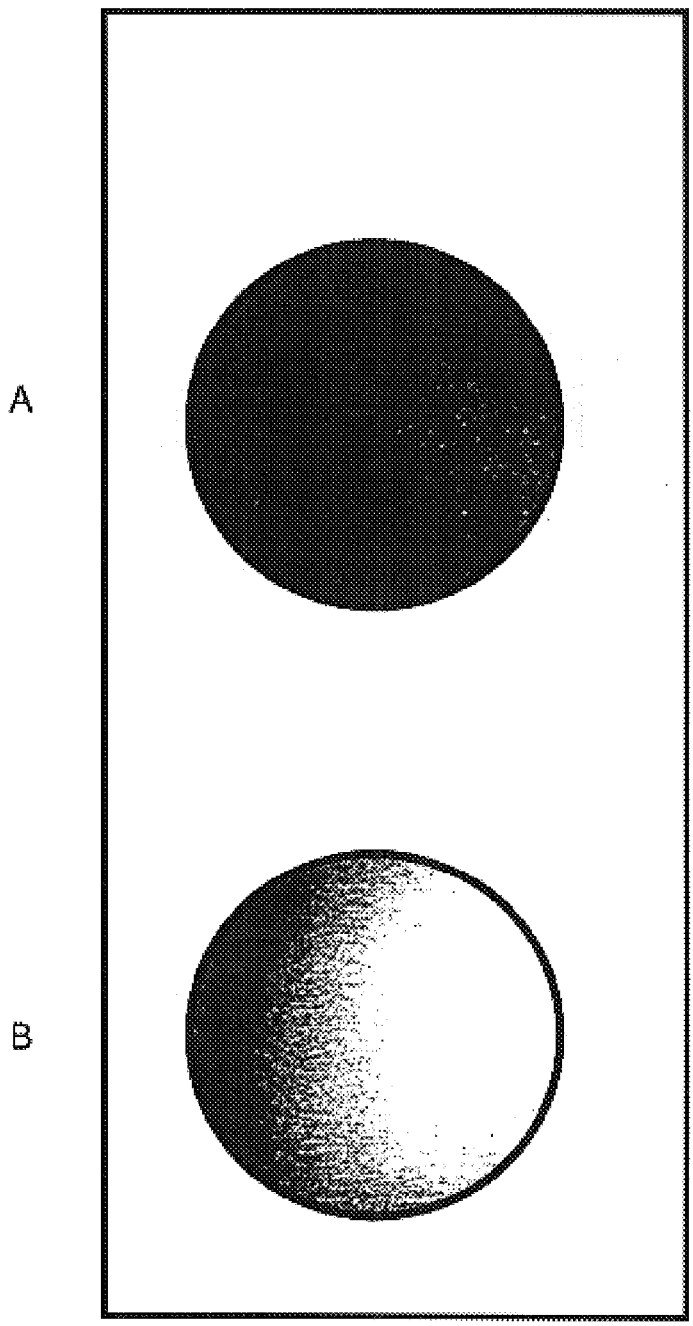
FIG. 1A shows a positive reaction in a particle agglutination test with saliva using KP90 and polystyrene particles.
FIG. 1B shows a negative reaction under the same conditions as in FIG. 1A.

Surprisingly, a highly reliable test has been developed based on the concept as outlined above. By using the method of the invention it is possible to monitor the different stages of a treatment of a mycobacterial disease.

Also, it is possible to determine whether an individual has been vaccinated for a mycobacterial disease, and for which mycobacterial disease. As not every organism infected with a Mycobacterium species shows the same reaction to said infection, a very reliable test is provided, in that a wide area of both antigens and antibodies that may be present can be covered in the test method.

The present method can be applied to any sample of body fluid of any human or animal individual of course, the most reliable results are obtained when a sample of a body fluid wherein the presence of a Mycobacterium species is most often encountered. Examples of suitable body fluids include serum, blood and excretion fluids, such as sputum, saliva, CSF (cerebrospinal fluid), or tear fluid. These body fluids can either be subjected to a method according to the invention directly, or they can undergo some form of pretreatment. Usually, the body fluids will be diluted by dissolution in a buffer solution prior to the diagnostic test.

In a preferred embodiment, saliva or a solution or preparation thereof is subjected to a diagnostic test for identifying a Mycobacterium species. If necessary, the mucus-like structure of the saliva can be removed by a treatment with for instance xylomethasolin or by any other known method. The invention also encompasses a diagnostic test method for identifying a Mycobacterium species wherein a sample of saliva is contacted with at least one immuno-cross-reactive antigen component of a mycobacterial species, and/or at least one antibody which is capable of reacting with a mycobacterial antigen, detecting the presence of antigen-antibody complexes, and identifying the Mycobacterium species present in the saliva sample. Surprisingly, the high content of various enzymes in saliva does not disturb the reliability of the diagnostic test to any substantial extent. In the alternative, the effect of the enzymes on the outcome of the test can suitably be annulled.

The performance of a test on saliva has surprisingly proven to be very successful and reliable. Apparently, mycobacterial infections are sufficiently manifested in saliva. The collection and use of saliva has many advantages over the use of more conventional body fluids, such as serum or blood. It is relatively easy to collect, even under the difficult field conditions, that are often encountered in Third World countries where both tuberculosis and leprosy have high incidence. Furthermore, saliva is non-invasive, which raises compliance of individuals to be tested, requires minimal training to collect and has reduced biohazard risk in collection, transport and testing, in particular in areas where a high incidence of HIV-infections exists.

As has been set forth hereinabove, according to the present invention a sample of a body fluid is contacted with both an antigen or a preparation thereof and an antibody or a preparation thereof. Very good results have also been obtained with a test wherein a sample of a body fluid is contacted with only an antibody, which is capable of reacting with a mycobacterial antigen, or a preparation thereof. The inventions thus also encompasses a method for identifying a Mycobacterium species comprising the steps of contacting at least one antibody, which is capable of reacting with a mycobacterial antigen, detecting the presence of antibody-antigen complexes, which have been formed between said antibody and one or more antigen components of the Mycobacterium species, and identifying the Mycobacterium species present in said body fluid sample.

In accordance with the invention, it is possible to contact a body fluid sample first with the antigen and subsequently with the antibody or vice versa. It is preferred, however, that the sample of a body fluid is contacted with the antigen and the antibody simultaneously. This can, for instance, be done by passing the body fluid sample by two surfaces, to one of which the antigen or the preparation thereof has been bound, and to the other of which the antibody or the preparation thereof has been bound. On the basis of this principle, the skilled person will be able to develop various ways of performing the diagnostic test. It will be apparent that when the method is chosen such that the antigen or the preparation thereof and the antibody or the preparation thereof are in contact with one another, the antigens and antibodies used have to be chosen such that they do not react with each other.

The at least one immuno-cross-reactive antigen component may comprise the total or a fraction of the components of Mycobacterium or the total or a fraction of the culture medium of *Mycobacterium*. In principle, any fraction of Mycobacterium or a culture medium thereof can be used. Such a fraction can be obtained in a conventional manner, and is advantageously separated by electrophoresis prior to the method according to the invention as has been described in WO-A-94/14069 to provide a banding pattern after the test has been performed. Usually, the antigen component will mainly comprise lipo-polysaccharides. However, often proteins will also be present. According to the invention, both lipo-polysaccharides and proteins, having antigen action, can be used separately or combined.

Preferred antigen components are chosen from the non-exhaustive group of KATG, MPT63 (=18 kD), MPT64 (=24 kD), MPT51, MTC28, Ag85a (=30–31 kD), Ag85b (=Ag6), Ag85c, Ag5 (=CIE Ag78 and=38kD), DES, MPB70,80 (=22/23 kD), Lipoologosaccharide (LOS), lipoarabinomannan (LAM), PMB67 (67 kD), Isocitrated dehydrogenase, Malate dehydrogynase, 2,3-diacyl-trehalose (DAT), Phenolicglycolipid (PGL), ESAT6 (=6 kD), hsp70=DnaK= Ag63 (=71kD), CIE Ag82=GroEL and homologues (=65 kD), GroES and homologues=BCGa (=10 kD), Antigen60, as well as those having molecular weights of 6 kD, 10/12 kD, 16 kD, (often referred to as 14 kD), 18 kD, 19 kD, 21 kD, 22 kD, 23 kD, 24 kD, 28 kD, 29 kD, 30 kD, 30 kD, region 32 kD, 33 kD, 34 kD, 36 kD, 38 kD, 42 kD, 50-55 kD, 60 kD, 65 kD, 67 kD, 71 kD, 88 kD, and 95 kD.

Preferably, the at least one immuno-cross-reactive antigen component comprises a KP90, KS90, antigen6, KP100, or SP100 fraction, or a fraction of a culture medium of a preparation of a Mycobacterium species. It has been found that these antigen preparation provide very reliable test results. Moreover, they are sufficiently stable to be stored for a prolonged period of time without affecting the reliability of the diagnostic test.

The at least one antibody for a mycobacterial species with which the sample of a body fluid is contacted in accordance with the invention, can be any antibody which is capable of reacting with a certain mycobacterial antigen. Such an antibody or a preparation thereof can be obtained in a manner known to the skilled artisan. According to the invention, it is preferred to use monoclonal antibodies, although the use of polyclonal antibodies has also proven to be suitable. Preferably, IgG, IgA, IgM or a combination thereof is used as the antibody. These antibodies have proven to be very convenient to handle in a diagnostic test and lead to very satisfying results.

In a preferred embodiment, the at least one immuno-cross-reactive antigen component or the at least one antibody for a mycobacterial species is immobilized on a support. Both non-solid supports and solid supports can be used. Preferably, a solid support is used.

Particularly preferred is the embodiment wherein both the antigen component and the antibody are immobilized on a support. When steps a) and b) are performed simultaneously, a particularly useful test has proven to be based on an embodiment of the invention wherein the antigen component and the antibody are immobilized on the same support. As has been stated above, in that case it is necessary that the antibody does not react with the at least one immuno-cross-reactive antigen component. It is advantageous to provide a layer of the at least one immuno-cross-reactive antigen component on top of a layer of the at least one antibody, or vice versa. Preferably, first a layer of the at least one immuno-cross-reactive antigen component is applied to the solid support, and then a layer of the at least one antibody is applied thereon.

The at least one immuno-cross-reactive antigen component will generally be used in a concentration from 0.1 to 20 $\mu$g/ml, and preferably from 1 to 10 $\mu$g/ml. When the antigen component is applied to a support, the amount of said component will depend on the test and the support chosen. The at least one antibody will generally be used in a concentration from 0.1 to 20 $\mu$g/ml, and preferably be from 1 to 10 $\mu$g/ml. When the antibody component is applied to a support, the amount of said component will depend on the test and the support chosen. The ratio wherein the at least one immuno-cross-reactive antigen component and the at least one antibody are used, will usually be of from 1:10 to 10:1, preferably from 1:2 to 2:1.

Preferred solid supports are chosen from the non-exhaustive group consisting of membranes, such as nitro-cellulose membranes, dip-sticks, filters, spheres, granules and microtiter plates. The antigen component and or the antibody may be immobilized on these supports in a manner known in the art.

After the sample of the body fluid has been contacted with the at least one immuno-cross reactive antigen component and the at least one antibody, there may or may not have formed antibody-antigen complexes. These complexes can be of two types; either the antibody or the antigen component of these complexes will be from the body fluid. Both or just one type of these complexes may be present. The detecting of the two types of complexes can be carried out separately or together. Preferably, they are performed simultaneously. Suitable detecting methods are immunoblotting, as has been disclosed in WO-A-94/14069, as well as any of the usual direct and indirect labeling methods known in the art. Suitable labels can be chosen from the non-exhaustive group of biotin, biocytin, iminobiotin, digoxigenin, avidin, streptavidin, colloidal dye substances, fluorochromes, such as rhodamin, reducing substances, such as eosin or erythrosin, (colored) latex sols, carbon sols, metals, metal sols or other particulate sols, dansyl lysin, Infra Red Dyes, coumarines, enzymes, and iodide labels. Particularly preferred is the use of gold labels, colloid labels, latex sols, and enzymes. The use of these labels enable the performance of a method according to the invention in a so-called rapid test.

After the analysis, the Mycobacterium species can suitably be identified. Although any conventional identification procedure can be used, it is preferred that the Mycobacterium species is identified on the basis of one. or more reference patterns.

Of course, the invention also encompasses a diagnostic kit for use in a method as described hereinabove. The kit comprises a support, on which at least one immuno-cross reactive antigen component of a mycobacterial species and at least one antibody, which is capable of reacting with a mycobacterial antigen and which does not react with said at least one immuno-cross reactive antigen component, are bound, and means for detecting the presence of antigen-antibody complexes. The support is preferably chosen from the group of membranes, dip-sticks, filters, spheres, granules and microtiter plates. The means for detecting may comprise the means for detecting in a manner as described herein above.

The invention will now be elucidated by the following non-restrictive examples.

EXAMPLES

Preparation of KP90/KS90

KP90 was prepared from starting material made from crude mycobacterial mass as follows:

The mycobacteria were cultured in commercially available Sauton medium supplemented with 2 g $MgSO_4$, 8 g citric acid, 2 g $K_2HPO_4$, 16 g asparagine, 2 g ($Fe^+$) ammonium citrate, 240 ml glycerol. The bacteria were cultured under standard conditions. The cells were harvested by filtration of the culture medium with a 12 $\mu$m filter. The cells were subsequently resuspended in 20 ml PBS (phosphate-buffered salt solution) (pH 7.4) and the harvested cells were autoclaved under a pressure of 15 Psi for 20 minutes in order to deactivate and sterilize the bacteria. The thus obtained bacterial mass can be stored at $-80°$ C.

In order to determine the quantity of starting material a 1/100 dilution of the harvested A autoclaved suspension in PBS was made. The optical density thereof, measured at 420 nm ($O.D._{420}$) must be 0.1. If necessary the concentrated bacterial mass is supplemented with PBS (pH 7.4) until the correct O.D. is obtained. An $O.D._{420}$ of 0.1 indicates the presence of $7 \times 10^{11}$ bacteria per 30 ml, which is equivalent to 12 g wet weight of the bacterial mass.

For preparation of a crude mycobacterial extract 5 g wet weight of the bacterial mass was washed three times with PBS (pH 7.4). Centrifuging was then carried out at 3000×g until the mass precipitated. The pellet was suspended in 50 ml PBS and stirred carefully to reduce formation of lumps to a minimum. To prevent lump forming 0.05% Tween 80 was optionally added. In order to avoid bacterial contamination 3 mg penicillin/streptomycin was added to this solution. The concentration was then brought with PBS to 2 g wet weight/ml.

The bacterial mass was subsequently broken open using an automatic French-X-press or RIBI press (American Instruments Company, Trevenollab. Inc. Maryland). The buckets were pre-cooled overnight at $-20°$ C. Before use, the buckets were held in a mixture of ethanol and dry ice ($-20°$ C.). After the buckets were filled with 1 g bacterial mass per bucket of 5 ml and cooled at $-80°$ C. for 20 minutes, the buckets were placed in the French-X press and 12 tons of pressure were applied by pushing in the plunger of the press. The buckets were then removed and cooled again at $-80°$ C. for 20 minutes. The buckets were inverted and treated for the second time. 10 tons of pressure were applied the second time. Cooling and breaking were then repeated a number of times, normally about 5 times. The disrupted cells were eluted with a suitable volume of PBS and subsequently centrifuged at 4° C. at 300×g for 10 minutes in order to remove the unbroken bacteria with the sediment. The collected supernatant was then centrifuged at 4° C. and 145,000×g for 2 hours. The pellet was suspended in 0.1 M Tris-HC1 (pH 7.2), 0.01 M EDTA which contained 20 mM $MgSO_4.7H_2O$ in a concentration of about I g per 10 ml. 1 mg RNase and 1 mg DNase were added per 10 ml volume. Incubation then took place overnight at 4° C. with careful stirring. Incubation thereafter took place for 1 hour at 37° C. and the lysate was centrifuged at 300×g and 4° C. for 10 minutes in order to remove the last-remaining unbroken bacteria (this is further referred to as "starting material"). Starting material made from 1 gram lyophilized bacteria was centrifuged at 90,000×g at 4° C. for 2 hours. The pellet was washed two times with PBS. Between the washing steps the sample was sonicated for 6×30 seconds on ice with interruptions of 10 seconds and centrifuged at 90,000×g at 4° C. for 2 hours. The pellet was collected and resuspended in 10 ml 0.05 M Tris buffered saline (TBS) pH 7.4. The supernatants, designated as KS90, can also be used as antigen. The pellet was sonicated for 6×15 seconds on ice with interruptions of 10 seconds. This preparation is designated with the term KP90. After the protein concentration was determined, quantities of 1.7 ml were frozen at concentrations of 1 mg/ml in 25 mM TBS/50% glycerol and stored at −20° C. The following components have been shown to be present in KP90: LAM (++), 10 kD (+), 16 kD (+), 21 kD (+), 24 kD (?), 30 kD (+/−), 31 kD (−), 34 kD (+/−), 38 kD (−), 65 kD (++), and 95 kD (+)

Preparation of a Culture Fluid Fraction

After culturing *Mycobacterium tuberculosis* for 3 weeks, the bacteria were removed by centrifugation and filtration. Components from the culture fluid were precipitated by 0–45% ammonium sulphate precipitation. After centrifugation, the precipitate was dialyzed and further purified by ion exchange chromatography. This fraction is called antigen6. Further purification can be performed by hydrophobic interaction chromatography.

Preparation of Monoclonal Antibodies (MoAb)

IgG monoclonal antibodies were prepared according to the literature (Clin. Exp. Immunol. (1984) 58:511–521)

Preparation of Saliva

Saliva was collected using the Omni-Sal™ saliva collection device (Saliva Diagnostic Systems) and stored at −20° C. The tube contains 1 ml of a preservative solution. The pad is designed to hold 1 ml of fluid when saturated, resulting in a 1:2 dilution of saliva. Before use the saliva sample was pretreated with protease inhibitor and triton X and nonidet P40 (0.01%)

Preparation of Serum

Blood was obtained by venipuncture and processed to serum using standard methods.

EIA

Coat

Before coating KP90 was sonicated for 5×10 seconds on ice with 10 seconds interruptions. Microtiter plates were coated with KP90 in several dilutions in PBS pH8.0 for 22 hrs at 37° C., or with one or more MoAbs (IgG or IgM) against components of *M. tuberculosis* in several dilutions in PBS pH 8.0 overnight at 4° C. MoAbs that were tested were a.o.: a MoAb against a 38kD protein of *M. tuberculosis*, and a MoAb against LAM. Combination coatings of MoAbs and KP90 were made by coating first with KP90 and then with one or more MoAbs, or by first coating with KP90 on one half of the microtiter plate well, while the plate was placed under an angle followed by coating with one or more MoAbs after the plate was turned 180°.

After coating the plates were blocked with 3% BSA for 1 hour at room temperature dried at 37° C. and stored at 4° C.

Test

Sera were tested in a 1:200 and 1:400 dilution. Saliva samples were tested in several dilutions ranging from 1:1 to 1:100.

100 µl was pipetted into the coated wells of a microtiter plate and incubated for 1 hour at 37° C. Non-binding serum components are washed away in a washing step with PBS. A second incubation with a conjugate, either anti-Hu-IgA, or anti-Hu-IgM, labeled with peroxidase, or another MoAb against the same component of *M. tuberculosis* which is monitored labeled with peroxidase, or a combination of these two is performed for 1 hour at 37° C. Excess conjugate is then washed away.

Indication of the presence of human antibodies of the sub-type IgA or IgM binding specifically to KP90 and/or the presence of *M. tuberculosis* components in the sample takes place by adding TMB (tetramethylbenzidine) to the wells.

Binding enzyme results in the occurrence of a blue color which, after addition of a coloring stop solution, changes to yellow. This yellow color has an absorption maximum of 450 nm.

Interpretation of the test results takes place on the basis of the so-called cut-off sample. A test sample can be considered positive when the result found in the test scores higher than the cut-off sample. The cut-off sample is based on results with a large panel of positive and negative subjects.

Results

After performing the procedures described above under 'Test' and 'Coat', the results as shown in Table I were obtained regarding the presence of antibodies in saliva. For determining anti-KP90-IgA, a saliva dilution of 1:100 was find to be suitable. For determining anti-KP90-IgG, a saliva dilution of 1:20 appeared to be suitable. In Table I, samples 38, 39, 40, 44, 4,18, 25, 31, and 33 were TB-positive, whereas the other samples were TB-negative.

A combination of an anti-Mycobacterium IgA and IgG antibody detection is saliva, wherein different cut-offs are employed, has additional value in diagnostics. Also, testing saliva in combination with serum has been found to have additional value in Mycobacterium diagnostics.

TABLE I detection of anti-Mycobacterium IgA and IgG in saliva samples

| Saliva | IgA (saliva 1:100) OD450 | +/− bij OD CO=0,7 | IgG (saliva 1:20) OD 450 | +/− bij OD CO=0,22 |
|---|---|---|---|---|
| 1 | 0.689 | − | 0.074 | − |
| 2 | 0.345 | − | 0.064 | − |
| 3 | 0.302 | − | 0.050 | − |
| 5 | 0.321 | − | 0.065 | − |
| 6 | 0.462 | − | 0.063 | − |
| 7 | 0.141 | − | 0.071 | − |
| 9 | 0.509 | − | 0.075 | − |
| 10 | 0.609 | − | 0.066 | − |
| 12 | 0.446 | − | 0.162 | − |
| 15 | 0.173 | − | 0.054 | − |
| 16 | 0.335 | − | 0.108 | − |
| 22 | 0.561 | − | 0.100 | − |
| 23 | 0.389 | − | 0.096 | − |
| 28 | 0.177 | − | 0.064 | − |
| 32 | 0.305 | − | 0.178 | − |
| 34 | 0.683 | − | 0.173 | − |
| 35 | 0.55 | − | 0.213 | − |
| 36 | 0.567 | − | 0.070 | − |
| 38 | 0.742 | + | 0.234 | + |

TABLE I-continued detection of anti-Mycobacterium IgA and IgG in saliva samples

| Saliva | IgA (saliva 1:100) OD450 | +/− bij OD CO=0,7 | IgG (saliva 1:20) OD 450 | +/− bij OD CO=0,22 |
|---|---|---|---|---|
| 39 | 0.351 | − | 0.364 | + |
| 40 | 0.555 | − | 0.301 | + |
| 44 | 0.801 | + | 0.235 | + |
| 4 | 1.074 | + | 1.152 | + |
| 18 | 0.833 | + | 0.106 | − |
| 25 | 1.064 | + | 0.678 | + |
| 31 | 0.059 | − | 2.204 | + |
| 33 | 1.945 | + | 0.077 | − |

In order to determine the presence of LAM in saliva, saliva a was first prepared as described above. Additionally, 1 ml samples were dialyzed in order to remove triton and salt, whereafter they were freeze-dried and taken up in 200 µl PBS. Of the thus obtained samples, 100 µl was pipetted in each well of a microtiter plate provided with a coat as described above. Detection took place as described above using rabbit anti-*M. tuberculosis* antibodies, which were in their turn detected using anti-rabbit-IgG-peroxidase conjugate. The results are shown in Table II.

TABLE II detection of LAM in saliva

| Saliva | | OD1 | OD2 | mean |
|---|---|---|---|---|
| 1 | TB-positive | 0.924 | 0.97 | 0.947 |
| 2 | TB-positive | 0.737 | 0.79 | 0.764 |
| 3 | TB-positive | 0.472 | 0.453 | 0.463 |
| 4 | TB-positive | 0.722 | 0.734 | 0.728 |
| 5 | TB-positive | 0.439 | 0.431 | 0.435 |
| 6 | TB-positive | 0.599 | 0.603 | 0.601 |
| 7 | TB-positive | 0.72 | 0.693 | 0.707 |
| 8 | TB-positive | 0.69 | 0.565 | 0.628 |
| 9 | TB-positive | 0.643 | 0.669 | 0.656 |
| mean | | | | 0.659 |
| 10 | TB-negative | 0.289 | 0.285 | 0.287 |
| 11 | TB-negative | 0.353 | 0.338 | 0.346 |
| 12 | TB-negative | 0.294 | 0.293 | 0.294 |
| 13 | TB-negative | 0.296 | 0.294 | 0.295 |
| 14 | TB-negative | 0.298 | 0.297 | 0.298 |
| 15 | TB-negative | 0.315 | 0.309 | 0.312 |
| 16 | TB-negative | 0.35 | 0.34 | 0.345 |
| 17 | TB-negative | 0.353 | 0.344 | 0.349 |
| 18 | TB-negative | 0.253 | 0.261 | 0.257 |
| mean | | | | 0.309 |

Further, IgG, IgA, and LAM were detected in sputum samples analogous to what has been described above for saliva. Anti-*M. tuberculosis* antibodies were determined in sputum using KP90.

To detect antibodies in sputum, samples of sputum were diluted 1:20 or 1:25 (for IgG and IgM) or 1:100 (for IgA) in serum dilution buffer from the KREATECH IgA EIA kit. The samples were vigorously shaken for at least one hour. Subsequently, the samples were tested for the presence of anti-tuberculosis antibodies by ELISA as described above.

KP90 was coated on a microtiter plate. The cut off ratio was 0.8 for IgG and IgM and 0.6 for IgA with serum 8-59 as a reference to calculate the ratio. The results are shown in

TABLE III detection of antibodies in sputum

| Sputum | | IgG | IgA | IgM |
|---|---|---|---|---|
| 1 | TB-negative | negative | positive | negative |
| 2 | TB-negative | negative | positive | negative |
| 3 | TB-negative | negative | negative | negative |
| 4 | TB-negative | negative | negative | negative |
| 5 | TB-negative | negative | positive | negative |
| 6 | TB-negative | negative | negative | negative |
| 7 | TB-negative | negative | negative | negative |
| 8 | TB-negative | negative | negative | negative |
| 9 | TB-positive | positive | positive | positive |
| 10 | TB-positive | positive | negative | positive |
| 11 | TB-positive | positive | negative | negative |
| 12 | TB-positive | negative | positive | positive |

Western Blot

Gelelectrophoresis and preparation of membrane for assays was performed as described in WO-A-94/14069, page 13 under point 2.

Strips were incubated with 1:100 or 1:200 diluted human serum or saliva collected with an Omni-Sal device dilutions ranging from 1:1 to 1:100.

For the detection of antibodies in serum and saliva immunodetection was performed as described in WO-A-94/14069.

Dot Blot Assay

Antigen (KP90) 1–10 µg/ml and MoAb 0.5–5 µg/ml were spotted separately onto nitrocellulose membrane. The membrane (blocked or unblocked with BSA) was incubated with serum (1:200 dilution) or saliva sample (1:1–1:100 dilution) in PBS/tween/BSA for 1 hour at room temperature. After washing the membrane with PBS/tween the membrane was incubated incubation with conjugate:

1. indirect label:
   a combination of anti-Hu-IgA or anti-Hu-IgG labeled with peroxidase and a MoAb (IgG or IgM) against the same component of *M. tuberculosis* which is monitored labeled with peroxidase. Detection was performed using AEC substrate (0.8% 3-amino-9-ethylcarbazole in dimethylformamide) 1:10 diluted in AEC buffer (50 mM Acetate Buffer, pH5.0, 0.1% ureumperoxide), DAB (3,3'-diamino-benzidine tetrahydrochloride) using standard methods, or the ECL detection system of Amersham.

2. direct label:
   a combination of anti-human-IgA or anti-human-IgG labeled with gold and a MoAb (IgG) against the same component of *M. tuberculosis*, which is monitored, labeled with gold. The IgA-gold conjugate was obtained commercially or made as described in e.g. WO-A-96/35696. The MoAb-gold conjugate was made as follows: The gold particles were obtained commercially. The conjugate was made according to standard procedures or in the case of platinum-based linker as described in e.g. WO-A-96/35696.

Rapid Strip Test

Antigen (KP90) 1–10 µg/ml and one or more MoAbs (IgG) 0.5–5 µg/ml are immobilized on different lanes on nitrocellulose membrane. A control lane depending on the Ab which is detected (anti-IgA or anti-IgG/proteinA) is also applied above the other lines. The nitrocellulose is used blocked with 0.1% BSA or unblocked. On a attached absorbent pad anti-IgA-gold conjugate and MoAb-gold conjugate (Moab against the same antigen as the immobilized MoAb but recognizing another determinant) are dried. The IgA-gold conjugate was obtained commercially or made as described in WO-A-96/35696. The MoAb-gold conjugate was made as described above. The sample (serum or saliva) is diluted in 1 ml PBS (pH 7.4) in an glass tube. The test strip is then dropped into the tube with the absorbent pad downwards. After 15 min to 2 hours, when the control line was colored, the results were determined.

Second procedure: Antigen (KP90) 1–10 µg/ml and one or more MoAbs (IgG) 0.5–5 µg/ml are immobilized on different lanes on nitrocellulose membrane (see FIG. 1). A control lane depending on the Ab which is detected (anti-IgA or anti-IgG/proteinA) is also applied above the other lines. An absorbent pad was attached. The whole sample was labeled with gold conjugate through a platinum based linker (see e.g. WO-A-96/35696). Then the strip was dropped into the sample with the absorbent pad downwards. After 15 min to 2 hours, when the control line was colored, the results were determined.

Agglutination Test
Coating

The latex particles are washed several times with Borate (pH 8.5) or PBS, by filtration, or by use of ion-exchange resins depending on the quantity needed. Antigen (KP90 or antigen6) or antibody are coated on latex particles by incubating, for 1–16 hours at 37° C., 20° C. or 4° C., 1 ml of 1% suspension of the appropriate particles in Borate (pH 8.5) or PBS containing 0.01% tween-20 and a final protein concentration up to 5 mg/ml. Subsequently the latex is centrifuged and the supernatant containing any unabsorbed ligand is discarded. After several washing steps (see above) the coated latex is re-suspended in MES buffer containing 0.1% BSA and can be used in a latex agglutination test or stored at +4° C.

Agglutination

The coated latex particles are mixed in several dilutions with serum or saliva sample in a drop on a glass slide. Agglutination is assayed after 1 at room temperature to 16 hours at +4° C. incubation time. The agglutination can be scored by eye (floc appearance) or after filtration of the mixture. In the latter case a pore size of the membrane is chosen which allows non agglutinated latex particles to pass and retains agglutinated particles. By using colored particles the membrane is colored in case of a positive reaction.

By using different colored latex particle for antigen (KP90 or antigen6) and antibody both reactions can be monitored separately.

Results

Serum was tested in accordance with the above procedure using KP90 and polystyrene particles. The incubation time of the test was from 5 minutes at room temperature. The results are shown in FIG. 1. FIG. 1A shows a positive reaction, whereas FIG. 1B shows a negative reaction.

What is claimed is:

1. A method for identifying a *Mycobacterium tuberculosis* or *Mycobacterium leprae* as responsible for a mycobacterial infection comprising the steps of:
   a) contacting at least one immuno-cross reactive antigen component of *Mycobacterium tuberculosis* or *Mycobacterium leprae* with a sample of a body fluid of a human or animal;
   b) contacting at least one anti-*Mycobacterium tuberculosis* or anti-*Mycobacterium leprae* antibody, which is capable of reacting with an antigen of the Mycobacterium species, with said body fluid sample;
   c) detecting the presence of antigen-antibody complexes formed in step a) and step b);
      wherein the antigen-antibody complexes are characteristic of the particular Mycobacterium species;
      wherein the immuno-cross reactive antigen component and the antibody do not react with each other;
      and thereby identifying the Mycobacterium species responsible for the mycobacterial infection.

2. A method according to claim 1, wherein the sample of a body fluid is chosen from the group consisting of serum, blood and excretion fluids, and solutions or preparations thereof.

3. A method according to claim 1, wherein the immuno-cross-reactive antigen component is bound to a support.

4. A method according to claim 1, wherein the antibody which reacts with a mycobacterial antigen is bound to a support.

5. A method according to claim 1 wherein steps a) and b) are performed simultaneously.

6. A method according to claim 1, wherein the immuno-cross-reactive antigen component and the antibody for a mycobacterial species are bound to the same solid support, and wherein said antibody does not react with the immuno-cross-reactive antigen component.

7. A method according to claim 6, wherein the support is chosen from the group consisting of membranes, dip-sticks, filters, spheres, granules and microtiter plates.

8. A method according to claim 1, wherein the antibody which reacts with a mycobacterial antigen is a monoclonal antibody.

9. A method according to claim 1, wherein the detecting the presence of antigen antibody complexes is performed by using an indirect or direct labeling method.

10. A method according to claim 1, wherein the detecting is performed by using a label chosen from the group of biotin, biocytin, iminobiotin, digoxigenin, avidin, streptavidin, a colloidal dye substance, a fluorochromes, a reducing substance, dansyl lysine, an Infra Red Dye, coumarin, an enzyme, and an iodide label.

11. A method according to claim 1, wherein the Mycobacterium species is identified on the basis of one or more reference patterns.

12. A method according to claim 1, wherein the immuno-cross reactive antigen component comprises the total of a preparation of *Mycobacterium tuberculosis*, or of *Mycobacterium leprae*, or the culture medium of *Mycobacterium tuberculosis*, or of *Mycobacterium leprae*.

13. A method according to claim 1, wherein the immuno-cross reactive antigen component comprises a KP90, KS90, antigen6, KP100 or Sp100 fraction of a total preparation of a *Mycobacterium tuberculosis*, or a suitable fraction of a culture medium of *Mycobacterium tuberculosis*.

14. A method according to claim 1, wherein the antibody which reacts with a mycobacterial antigen comprises IgG, TgA, IgM or any combination thereof.

15. A diagnostic kit comprising a support, on which at least one immuno-cross reactive antigen component of *Mycobacterium tuberculosis*, or of *Mycobacterium leprae* and at least one *Mycobacterium tuberculosis* or *Mycobacterium leprae* antibody which does not react with said immuno-cross reactive antigen component, are bound, and means for detecting the presence of antigen-antibody complexes.

16. A diagnostic kit according to claim 15, wherein the support is chosen from the group consisting of membranes, dip-sticks, filters, spheres, granules and microtiter plates.

17. The method according to claim 2 wherein the excretion fluid is sputum, saliva, CSF (cerebrospinal fluid), or tear fluid.

18. The method according to claim 1, wherein the detection step is by detecting agglutination.

19. The method according to claim 18 wherein the immuno-cross reactive antigen component or the antibody, or both, are immobilized on particles or beads and the detection step is by detecting agglutination of the particles or beads.

20. The method according to claim 19, wherein the particles or beads bearing the immuno-cross reactive antigen component and the antibody are colored.

21. The method according to claim 20, wherein both the particles or beads bearing the immuno-cross reactive antigen component and the particles or beads bearing antibody are colored.

22. The method according to claim 21, wherein the particles or beads bearing the immuno-cross reactive antigen component and the particles or beads bearing antibody are differently colored.

23. The method according to claim 1, wherein at least one immuno-cross reactive antigen component is selected from the group consisting of KATG; MPT63 (18kD); MPT64 (24kD); MPT51; MTC28; Ag85a (30–31kD); Ag85b (Ag6); Ag85c; Ag5 (CIE, Ag78 and 38kD); DES; MPB70/80; lipooligosaccharide (LOS); lipoarabinomannan (LAM); PMB67 (67kD); isocitrate debydrogenase; malate dehydrogenase; 2,3-diacyl-trehalose (DA []); phenolicglycolipid (PGL); ESAT6 (6kD); hsp70 (DnaK, Ag63, 71kD); CIE (Ag82, GroES and homologues, BCGa, 10kD); antigen 60; an antigen having one of the following molecular weights: 6 kD, 10/12 kD, 16 kD (often referred to as 14 kD), 18 kD, 19 kD, 21 kD, 22 kD, 23 kD, 24 kD, 28 kD, 29 k 30 kD, 30 kD region, 32 kD, 33 kD, 34 kD 36 kD, 38 kD, 42 kD, 50–55 kD, 60 kD, 65 kD, 67 kD, 71 kD, 88 kD and 95 kD.

24. The method according to claim 1, wherein the antibody is a monoclonal antibody.

25. The method according to claim 1, wherein the antibody is a polyclonal antibody.

26. The method according to claim 3, wherein the support is a non-solid support.

27. The method according to claim 26, wherein the antibody and the immuno-cross reactive antigen component are each separately immobilized on the same non-solid support.

28. The method according to claim 3, wherein the antibody is immobilized on the support as a layer on op of a layer of the immuno-cross reactive antigen component.

29. The method according to claim 3, wherein the immuno-cross reactive antigen component is immobilized on the support as a layer on top of a layer of the antibody.

30. The method according to claim 1, wherein the cross reactive antigen component is immobilized by coating the support at a concentration of cross reactive antigen component of between about 0.1 micrograms per milliliter and about 20 micrograms per milliliter.

31. The method according to claim 30, wherein the cross reactive antigen component is immobilized by coating the support at a concentration of cross reactive antigen component of between about 1 micrograms per milliliter and about 10 micrograms per milliliter.

32. The method according to claim 1, wherein the antibody is immobilized by coating the support at a dilution of between about 1:10 and 10:1.

33. The method according to claim 32, wherein the antibody is immobilized by coating the support at a dilution of between about 1:2 and 2:1.

34. The method according to claim 1, wherein the immuno-cross reactive antigen component comprises one or more of the following: lipoarabinomannan (LAM); and antigens of molecular weights: 10 Kd 21 Kd, 30 Kd, 34 Kd, 65 Kd and 95 Kd.

35. The method according to claim 1, wherein the Mycobacterium species of the immuno-cross reactive component of step a) is *Mycobacterium tuberculosis* and the antibody of step b) is an anti-*Mycobacterium tuberculosis* antibody.

36. The method according to claim 1, wherein the immuno-cross reacting antigen component and the antibody are immobilized and separated from each other.

37. The method according to claim 36, wherein the immuno-cross reacting antigen component and the antibody are each bound to a solid or non-solid support.

38. The method according to claim 37, wherein the bound immuno-cross reacting antigen component and the bound antibody are separated on the surface of the solid support.

39. The method according to claim 1, wherein the Mycobacterium species responsible for the mycobacterial infection is identified on the basis of a reference pattern.

40. The method according to claim 1, wherein the Mycobacterium species responsible for the mycobacterial infection is identified on the basis of a cut-off sample.

41. The method according to claim 40, wherein the Mycobacterium species responsible for the mycobacterial infection is identified in an enzyme-linked immunoassay (EIA).

42. The method according to claim 1, wherein first step a) and subsequently step b) are performed or vice versa.

* * * * *

UNITED STATES PATENT AND TRADEMARK OFFICE
CERTIFICATE OF CORRECTION

PATENT NO. : 6,733,983 B1  Page 1 of 1
DATED : May 11, 2004
INVENTOR(S) : Houthoff et al.

It is certified that error appears in the above-identified patent and that said Letters Patent is hereby corrected as shown below:

Column 3,
Line 18, now reads "individual of course, ..." and should read -- individual. Of course, ... --

Column 6,
Line 2, now reads "one. or more, ..." and should read -- one or more... --
Line 36, now reads "harvested A autocloaved ...", and should read -- harvested autoclave ... --

Column 9,
Line 19, now reads "saliva a was", and should read -- saliva was... --
Line 67, now reads "shown in", and should read -- shown in Table III. --

Column 12,
Line 33, now reads "a fluorochromes ..." and should read -- a fluorochrome ... --
Line 47, now reads "preparation of a Mycobacterium, ...", and should read -- preparation of Mycobacterium ... --
Line 51, now reads "IgG, TgA, IgM", and should read -- IgG, IgA, IgM ... --

Column 13,
Line 15, now reads "bearing antibody ..." and should read -- bearing the antibody ... --
Line 23, now reads "debydrogenase...", and should read -- dehydrogenase ... --
Line 24, now reads "(DA[)...", and should read -- (DAT)... --
Line 43, now reads "on op...", and should read -- on top ... --

Signed and Sealed this

Tenth Day of August, 2004

JON W. DUDAS
*Acting Director of the United States Patent and Trademark Office*